United States Patent
Moenning et al.

(10) Patent No.: US 6,451,041 B1
(45) Date of Patent: *Sep. 17, 2002

(54) APPARATUS FOR PROTECTING A PORT SITE OPENING IN THE WALL OF A BODY CAVITY AND REDUCING ELECTROSURGICAL INJURIES

(75) Inventors: Stephen P. Moenning, 1940 Jamaica Way, Punta Gorda, FL (US) 33950; Javier Castaneda, Miami, FL (US); Matthew A. Palmer, Miami, FL (US)

(73) Assignee: Stephen P. Moenning, Punta Gorda, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/265,481

(22) Filed: Mar. 9, 1999

Related U.S. Application Data

(63) Continuation-in-part of application No. 08/954,910, filed on Oct. 21, 1997, now Pat. No. 5,941,898, which is a continuation-in-part of application No. 08/656,430, filed on May 30, 1996, now Pat. No. 5,725,553, which is a continuation-in-part of application No. 08/608,644, filed on Feb. 29, 1996, now Pat. No. 5,766,220.

(51) Int. Cl.$^7$ .............................. A61B 17/34

(52) U.S. Cl. ................... 606/185; 604/164.04

(58) Field of Search .................. 606/185, 190, 606/191, 198, 108; 604/264, 164.04, 164.11, 164.09, 174; 600/204

(56) References Cited

U.S. PATENT DOCUMENTS

| 3,713,447 A | 1/1973 | Adair | 128/347 |
|---|---|---|---|
| 4,535,773 A | 8/1985 | Yoon | 604/51 |
| 4,601,710 A | 7/1986 | Moll | 604/165 |
| 4,682,981 A | 7/1987 | Suzuki et al. | 604/158 |
| 4,874,378 A | 10/1989 | Hillstead | 604/167 |

(List continued on next page.)

FOREIGN PATENT DOCUMENTS

| EP | 0 542428 A1 | 5/1993 | A61B/17/34 |
|---|---|---|---|
| WO | WO 95/24864 | 9/1995 | A61B/17/04 |

*Primary Examiner*—Michael H. Thaler
(74) *Attorney, Agent, or Firm*—Wood, Herron & Evans, L.L.P.

(57) ABSTRACT

A medical apparatus is disclosed. The medical apparatus includes a trocar assembly having a cannula and a trocar, wherein (1) the cannula has (i) a lumen defined therein and (ii) a length $L_1$, (2) the trocar is positionable between a first trocar position and a second trocar position, (3) the trocar is positioned within the lumen of the cannula when the trocar is positioned at the first trocar position, and (4) the trocar is completely removed from the lumen of the cannula when the trocar is positioned at the second trocar position. The medical apparatus also includes a sleeve having (i) a passageway extending therethrough, (ii) a sealing member extending therefrom, and (iii) a length $L_2$, wherein (1) the cannula is positionable between a first cannula position and a second cannula position, (2) the cannula is positioned within the passageway of the sleeve when the cannula is positioned at the first cannula position, (3) the cannula is completely removed from the passageway of the sleeve when the cannula is positioned at the second cannula position, and (4) the length $L_1$ of the cannula is greater than the length $L_2$ of the sleeve such that a portion of the cannula extends out of the passageway of the sleeve when the cannula is positioned at the first cannula position. An associated medical procedure which utilizes the medical apparatus is also disclosed.

14 Claims, 10 Drawing Sheets

U.S. PATENT DOCUMENTS

| | | | | |
|---|---|---|---|---|
| 4,931,042 | A | 6/1990 | Holmes et al. | 604/164 |
| 4,969,870 | A | 11/1990 | Kramer et al. | 604/51 |
| 5,066,288 | A | 11/1991 | Deniega et al. | 604/274 |
| 5,073,169 | A | 12/1991 | Raiken | 604/180 |
| 5,114,407 | A | 5/1992 | Burbank | 604/164 |
| 5,122,122 | A | 6/1992 | Allgood | 604/174 |
| 5,147,316 | A | 9/1992 | Castillenti | 604/164 |
| 5,152,754 | A | 10/1992 | Plyley et al. | 604/164 |
| 5,176,648 | A | 1/1993 | Holmes et al. | 604/164 |
| 5,203,773 | A | 4/1993 | Green | 604/104 |
| 5,215,531 | A | 6/1993 | Maxson et al. | 604/180 |
| 5,217,451 | A | 6/1993 | Freitas | 606/1 |
| 5,290,249 | A | 3/1994 | Foster et al. | 604/174 |
| 5,318,580 | A | 6/1994 | Gresl, Jr. | 606/185 |
| 5,330,497 | A | 7/1994 | Freitas et al. | 606/185 |
| 5,338,305 | A | 8/1994 | Plyley et al. | 604/164 |
| 5,342,382 | A | 8/1994 | Brinkerhoff et al. | 606/184 |
| 5,345,927 | A | 9/1994 | Bonutti | 128/20 |
| 5,346,459 | A | 9/1994 | Allen | 606/185 |
| 5,350,393 | A | 9/1994 | Yoon | 606/185 |
| 5,354,283 | A | 10/1994 | Bark et al. | 604/180 |
| 5,356,421 | A * | 10/1994 | Castro | 606/185 |
| 5,364,367 | A | 11/1994 | Banks et al. | 604/174 |
| 5,366,446 | A | 11/1994 | Tal et al. | 604/110 |
| 5,366,478 | A | 11/1994 | Brinkerhoff et al. | 660/213 |
| 5,368,545 | A | 11/1994 | Schaller et al. | 600/37 |
| 5,370,647 | A | 12/1994 | Graber et al. | 606/127 |
| 5,375,588 | A | 12/1994 | Yoon | 128/4 |
| 5,391,156 | A | 2/1995 | Hildwein et al. | 604/174 |
| 5,405,330 | A | 4/1995 | Zunitch et al. | 604/240 |
| 5,443,449 | A | 8/1995 | Buelna | 604/105 |
| 5,445,615 | A * | 8/1995 | Yoon | 604/96 |
| 5,467,762 | A * | 11/1995 | Sauer et al. | 606/185 |
| 5,540,648 | A | 7/1996 | Yoon | 600/114 |
| 5,540,675 | A | 7/1996 | Hasson | 606/1 |
| 5,549,595 | A | 8/1996 | Freitas | 606/1 |
| 5,634,937 | A | 6/1997 | Mollenauer et al. | 606/213 |
| 5,637,097 | A | 6/1997 | Yoon | 604/174 |
| 5,658,272 | A | 8/1997 | Hasson | 606/1 |
| 5,782,813 | A | 7/1998 | Yoon | 604/174 |
| 5,830,232 | A | 11/1998 | Hasson | 606/213 |
| 5,941,898 | A * | 8/1999 | Moenning et al. | 606/213 |

* cited by examiner

APPARATUS FOR PROTECTING A PORT SITE OPENING IN THE WALL OF A BODY CAVITY AND REDUCING ELECTROSURGICAL INJURIES

CROSS REFERENCE

This application is a continuation-in-part of application No. 08/954,910, filed Oct. 21, 1997, now U.S. Pat. No. 5,941,898, which is a continuation-in-part of application Ser. No. 08/656,430, filed May 30, 1996, now U.S. Pat. No. 5,725,553, which is a continuation-in-part of application Ser. No. 08/608,644, filed Feb. 29, 1996, now U.S. Pat. No. 5,766,220.

BACKGROUND OF THE INVENTION

The present invention generally relates to a medical apparatus and procedure. The present invention particularly relates to an apparatus and procedure for protecting a port site opening in the wall of a body cavity and preventing electrosurgical injuries caused by capacitive coupling.

Minimally invasive surgical techniques, such as laparoscopic surgery, typically include the use of a trocar assembly. A trocar assembly includes a trocar (sometimes referred to as an "obturator") positioned within the lumen of a cannula. The trocar and cannula are advanced through a body cavity wall so as to create a small hole or a port site wound therein. The trocar is then completely removed from the lumen of the cannula such that the cannula's lumen provides an entrance for laparoscopic instruments into the interior of the body cavity. The body cavity is then insufflated with an inert gas, such as $CO_2$, to provide easier access to the organs contained therein. Once the surgery is complete the cannula is completely removed from the port site wound to rapidly desufflate the body cavity.

Surgery performed by using minimally invasive techniques is generally associated with lower postoperative morbidity, shorter postoperative stay, less postoperative pain, decreased cost, and quicker recovery as compared to "open" or conventional surgical techniques [1,2,3,4]. Because of the aforementioned advantages, these minimally invasive techniques are being applied to an increasing variety of all surgical procedures. For example, laparoscopic procedures for the resection of malignancies have emerged. In particular, laparoscopic colectomy for carcinoma of the colon has been developed, and it has been reported that the initial results of these procedures have advantages over operations performed in the traditional open manner [5,6,15]. Moreover, it is hoped that the long term results of these procedures will be comparable, or better than, those performed in the traditional open manner.

However, the development of laparoscopic surgery for cancer has been hindered because of the major concern regarding the implantation of tumor cells in the port site wound [2,3,6,7]. In fact, numerous port site recurrences have been documented in the medical literature heretofore, and subcutaneous metastases after laparoscopic resection of malignant tissue is associated with a decreased survival rate for patients who may have had a curative cancer [2,3,6,7]. Specifically, the medical literature reports that the incidence of tumor cell implantation ranges from as high as 20% to as low as 0%[8]. The studies generating the aforementioned data utilized highly skilled and experienced laparoscopic surgeons practicing at major university programs. However, in spite of utilizing highly skilled and experienced laparoscopic surgeons, the data indicates that the incidence of tumor cell implantation in the surgical wound is greater when employing laparoscopic techniques as compared to when conventional surgical techniques are used (i.e. 0.6% implantation incidence for conventional techniques [9] compared to 1% incidence for laparoscopic techniques [10]).

Several mechanisms may be responsible for the above discussed implantation of tumor cells in the port site wound. For example, minimally invasive surgical techniques for treating cancer require the insertion and removal of laparoscopic instruments or cameras through the lumen of the cannula. In addition, these surgical techniques require that the cannula itself be moved relative to the port site wound such that the cannula is advanced further into, or withdrawn from, the body cavity [11]. Moving the cannula in the above described manner facilitates a surgeon's ability to optimally locate instruments within the body cavity thereby helping to ensure the successful completion of the medical procedure. However, the aforementioned manipulations of the laparoscopic instruments and cannula may result in the exposure of the port site wound to exfoliated cancer cells which creates a risk of implanting tumor cells in the walls of the port site wound [11,12]. In particular, exfoliated cancer cells may adhere to and thus contaminate a portion of the exterior surface of the cannula [11,12]. The contaminated portion of the exterior surface of the cannula may then be advanced into contact with the port site wound during insertion and removal from the port site wound [11,12]. This contact may dislodge the exfoliated cancer cells from the exterior surface of the cannula and thus cause the exfoliated cancer cells to be implanted in the port site wound [11,12].

Furthermore, studies have shown that a physician may undergo a significant learning curve before becoming proficient in the performance of laparoscopic surgery, such as cancer surgery [3,13]. As a result, a relatively inexperienced surgeon may have a tendency to manipulate or handle a tumor to a greater degree during a surgical procedure than an experienced surgeon. In addition, an inexperienced surgeon may have a tendency to insert and withdraw an instrument through the lumen of the cannula a greater number of times than an experienced surgeon. The above described increased manipulation of the instrument or the tumor can result in a greater incidence of tumor cell implantation in the port site wound [11,12].

Regardless of how these cells contaminate the wound, once implanted therein, viable tumor cells can cause a subcutaneous metastases or "port/extraction site recurrence" after the resection of malignant tissue. These "port/extraction site recurrences" have delayed the advancement of laparoscopic cancer surgery [2,6,7,8,9,10,11,12]. Therefore, it is desirable to provide an apparatus which will protect a port site wound from tumor cell implantation while allowing a surgeon to optimally locate instruments within the body cavity for successful completion of the medical procedure.

Furthermore, laparoscopic surgery performed for general surgery, gynecological surgery, urological surgery, or any other intra-abdominal surgery is associated with a small but real incidence of port site wound infection [1]. The infecting bacteria causing these illnesses can contaminate the port site wound in the same manner as discussed above with regard to tumor cell contamination, and these infections can increase a patient's morbidity and consequently the length of a patient's hospital stay, thereby considerably increasing their hospital bill.

Moreover, the use of electrosurgical techniques are increasingly being used in conjunction with laparoscopic techniques. While the combination of electrosurgical and laparoscopic techniques has many advantages, it is recognized that potentially serious electrosurgical injuries can occur during these types of laparoscopic operations. In particular, the overall incidence of recognized electrosurgical injuries is between one and two patients per 1,000 operations [16]. However, the total incidence of these types of injuries (i.e. the sum of recognized and unrecognized injuries) may be significantly higher since the majority go unrecognized at the time of the electrical insult and commonly present three to seven days afterward with fever and pain in the abdomen. These injuries have significantly increased the cost of health care.

The pathophysiology of some of the electrosurgical injuries received during laparoscopic surgery appear to involve the property of capacitance [16]. A capacitor exists whenever a nonconductor separates two conductors. During minimally invasive surgery procedures a capacitor situation may be created by a surgical instrument. For example, the active electrode used in electrosurgical procedures is surrounded by nonconductive insulation, and the nonconductive insulation is surrounded by conductive metal cannula thereby creating a capacitor. The capacitor can create an electrostatic field between the two conductors (i.e. the active electrode and the metal cannula). As a result, a current in one conductor can, through the electrostatic field, induce a current in the second conductor. For example, an electrical current in the active electrode can induce an electrical current in the metal cannula.

Another surgical system uses a plastic cannula rather than a metal cannula. In a plastic cannula system the electrode is surrounded by insulation, which is then surrounded by a plastic cannula. The patient's conductive tissue completes the definition of a capacitor. In this situation, capacitance is reduced but not eliminated.

The worst situation with respect to problems caused by capacitance is one involving a "hybrid cannula system". This occurs when a metal cannula is held in place by a plastic anchor or "collar". The metal cannula still creates a capacitor with the active electrode, but the plastic collar around the metal cannula prevents the current from dissipating through the abdominal wall. This capacitively coupled current may exit to adjacent tissue on its way to the patient's return electrode. This can cause significant injury [17]. A recent study has shown that burns caused by such capacitive coupling may occur in vivo and result in serious injury to internal organs which can increase a patient's morbidity and even cause death [16].

As technology advances, new surgical procedures, such as remote laparoscopic surgery (i.e. robotic laparoscopic surgery), are being introduced and utilized in the field of minimally invasive surgery [14]. During use of these new surgical procedures the sensory feedback to the surgeon is decreased since robotic "arms" and "hands" (under the surgeon's control) manipulate the surgical instruments. The decrease in the surgeon's tactile sensory feedback can be a disadvantage when performing laparoscopic surgery for cancer. This is true since tactile feedback helps the surgeon avoid unnecessary manipulation of a tumor which may result in the implantation of tumor cells in the wall of the port site wound [2].

Therefore, in light of the above discussion, it is apparent that an apparatus which allows unrestricted movement of the cannula relative to the port site wound while preventing port site wound tumor cell implantation, reducing the incidence of port site wound infection, and preventing electrosurgical injuries, is desirable. The present invention provides such an apparatus in the form of a sleeve which protects the port site wound. One advantage the present invention has over the prior art is that it can be retrofit to existing trocar assembly technology. More specifically, the sleeve of the present invention can be used with trocar assemblies which are currently commercially available to laparoscopic surgeons. Another advantage the present invention has over the prior art is that it allows the cannula to be advanced into and withdrawn from the port site wound while still protecting the port site wound from contamination by tumor or other types of cells. Moreover, once attached, the described invention adds only a minimal amount of bulk to the diameter of the trocar assembly and prevents electrosurgical injuries.

TABLE OF REFERENCES CITED IN THE BACKGROUND

1. Lord et al., *Dis. Col. Rect.* 39(2):148 (1996)
2. Berman, *Important Advances in Oncology*1996, *Laparoscopic Resection for Colon Cancer Cause for Pause*, Vincent DeVita Ed., p. 231
3. Falk et al., *Dis. Col. Rect.* 36:28 (1993)
4. Liberman et al., *Surg. Endo.* 10:15 (1996)
5. Reiver et al., *Dis. Col. Rect.* 37:22 (Podium Abstract 1994)
6. Regier, *Gen. Surg. Lap. News* 8:1 (1995)
7. Greene, *Semin. Lap. Surg.* 2(3):153 (1995)
8. Kazemier, *Surg. Endo.* 9:216 (1995)
9. Reilly et al., *Dis. Col. Rect.* 39(2):200 (1996)
10. Jacquet et al., *Dis. Col. Rect.* 38(10):140 (1995)
11. Reymond et al., *Surg. Endo.* 11:902 (1997)
12. Allardyce et al., *Dis. Col. Rect.* 40(8):939 (1997)
13. Caushaj et al., *Dis. Col. Rect.* 37(4):21 (Podium Abstract 1994)
14. *Med. Simula. Train.*, 1(2):7, 12–13, 20–28 (1996)
15. Fleshman et al., *Dis. Col. Rect.* 39(1):15 (1996)
16. Nduka etal., *J. Amer. Col. Surg.* 179:161 (1994)
17. *Principles of Electrosurgery; Educational Booklet*, Valleylab Inc. Pfizer Hospital Products Group, Boulder, Colo., p. 13 (1995)

SUMMARY OF THE INVENTION

In accordance with one embodiment of the present invention, there is provided a medical apparatus which includes a trocar assembly having a cannula and a trocar, wherein (1) the cannula has (i) a lumen defined therein and (ii) a length $L_1$, (2) the trocar is positionable between a first trocar position and a second trocar position, (3) the trocar is positioned within the lumen of the cannula when the trocar is positioned at the first trocar position, and (4) the trocar is completely removed from the lumen of the cannula when the trocar is positioned at the second trocar position. The medical apparatus also includes a sleeve having (i) a passageway extending therethrough, (ii) a sealing member extending therefrom, and (iii) a length $L_2$, wherein (1) the cannula is positionable between a first cannula position and a second cannula position, (2) the cannula is positioned within the passageway of the sleeve when the cannula is positioned at the first cannula position, (3) the cannula is completely removed from the passageway of the sleeve when the cannula is positioned at the second cannula position, and (4) the length $L_1$ of the cannula is greater than the length $L_2$ of the sleeve such that a portion of the cannula extends out of the passageway of the sleeve when the cannula is positioned at the first cannula position.

Pursuant to another embodiment of the present invention, there is provided a medical procedure which includes the steps of creating an opening in a wall of a body cavity and advancing a medical apparatus through the opening and into the body cavity. The medical apparatus includes (1) a sleeve having (i) a passageway extending therethrough, (ii) a sealing member connected thereto, and (iii) a length $L_2$ and (2) a trocar assembly positioned within the passageway of the sleeve. The trocar assembly includes a cannula and a trocar, wherein (i) the cannula is completely removable from the passageway of the sleeve, (ii) the cannula has a lumen defined therein, (iii) the cannula has a length $L_1$, (iv) the trocar is completely removable from the lumen of the cannula, and (v) the length $L_1$ of the cannula is greater than the length $L_2$ of the sleeve such that a portion of the cannula extends out of the passageway of the sleeve when the cannula is positioned within the passageway of the sleeve. The medical procedure also includes the step of positioning the sealing member to contact an interior surface of the body cavity.

Pursuant to yet another embodiment of the present invention there is provided medical apparatus which is positionable within an opening defined in a wall of a body cavity. The medical apparatus includes a trocar assembly having a cannula and a trocar, wherein (1) the cannula has a lumen defined therein, (2) the trocar is positionable between a first trocar position and a second trocar position, (3) the trocar is positioned within the lumen of the cannula when the trocar is positioned at the first trocar position, and (4) the trocar is completely removed from the lumen of the cannula when the trocar is positioned at the second trocar position. The medical apparatus also includes a sleeve having (i) a passageway extending therethrough and (ii) a sealing member extending therefrom, wherein (1) the sealing member is movable between (i) a advancement orientation in which the sealing member is positioned to facilitate advancement of the sleeve into the opening and (ii) a sealing orientation in which the sealing member is positioned in contact with an interior surface of the wall of the body cavity which surrounds a space defined between the opening of the body cavity and the sleeve and (2) the cannula is positioned within the passageway of the sleeve such that the cannula is movable in an axial direction relative to the sleeve when the sealing member is in the sealing orientation.

It is therefore an object of the present invention to provide a new and useful medical apparatus and medical procedure.

It is another object of the present invention to provide an improved medical apparatus and medical procedure.

It is still another object of the present invention to provide a new and useful medical apparatus and medical procedure for protecting a port site wound from tumor cell implantation or contamination with an infectious agent.

It is another object of the present invention to provide an improved medical apparatus and medical procedure for protecting a port site wound from tumor cell implantation or contamination with an infectious agent.

It is also an object of the present invention to provide a medical apparatus for protecting a port site wound having a sleeve which can be used with trocar assemblies which are currently commercially available to laparoscopic surgeons.

It is still another object of the present invention to provide a medical apparatus for protecting a port site wound which adds only a minimal amount of bulk to the diameter of a trocar assembly.

It is yet another object of the present invention to provide a medical apparatus and medical procedure which continuously protects the port site wound from tumor cell implantation, or contamination with an infectious agent, during the movement of a cannula relative to the port site wound.

It is yet another object of the present invention to provide a medical apparatus and medical procedure which continuously protects the port site wound from tumor cell implantation, or contamination with an infectious agent, during robotic surgery.

It is still another object of the present invention to provide a medical apparatus and medical procedure which prevents electrosurgical injuries caused by capacitive coupling.

The above and other objects, features, and advantages of the present invention will become apparent from the following description and attached drawings.

DETAILED DESCRIPTION OF THE PREFERRED EMBODIMENT

Figure 1:
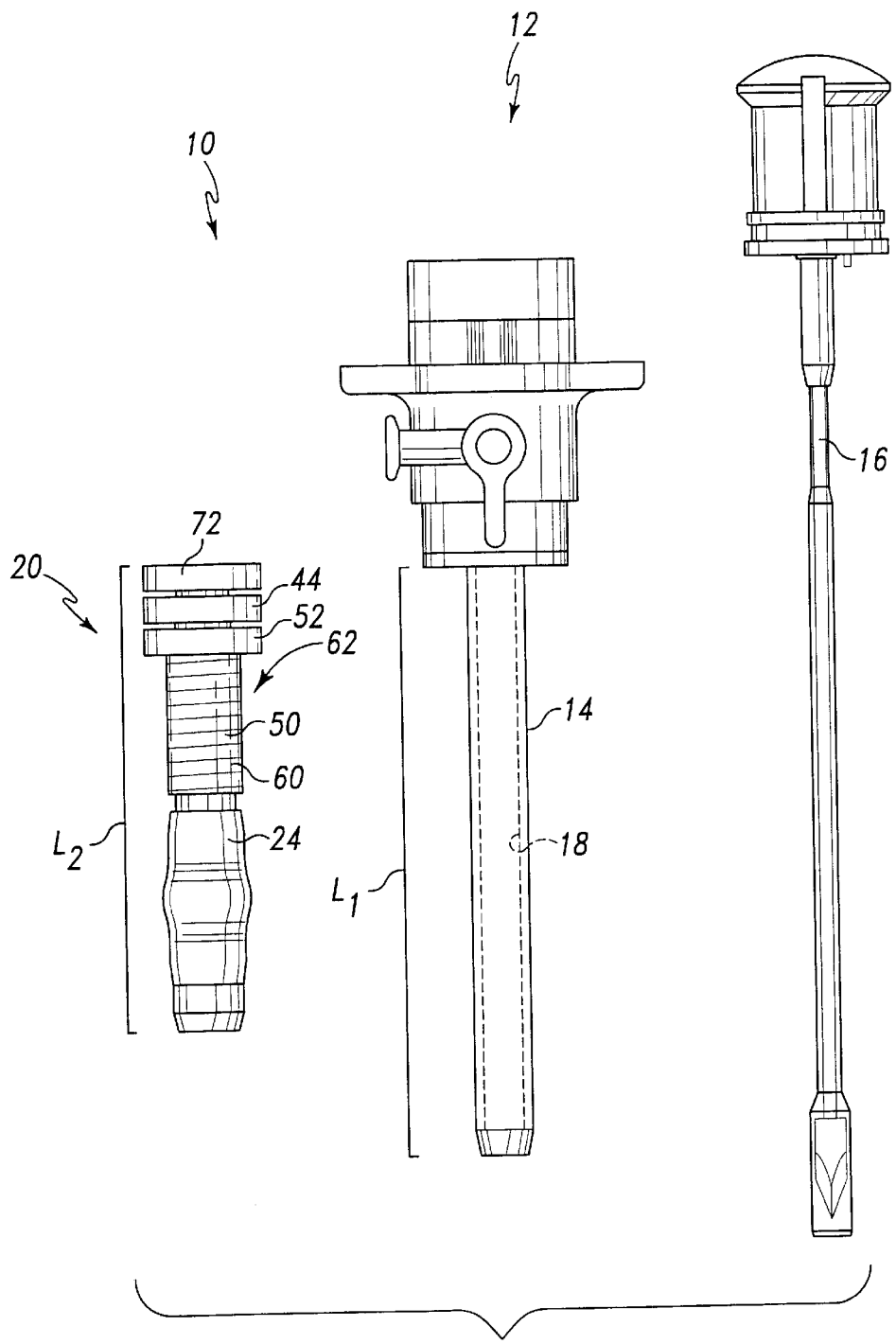
FIG. 1 is a side elevational view of the components of a medical apparatus which incorporates the features of the present invention therein.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 3:
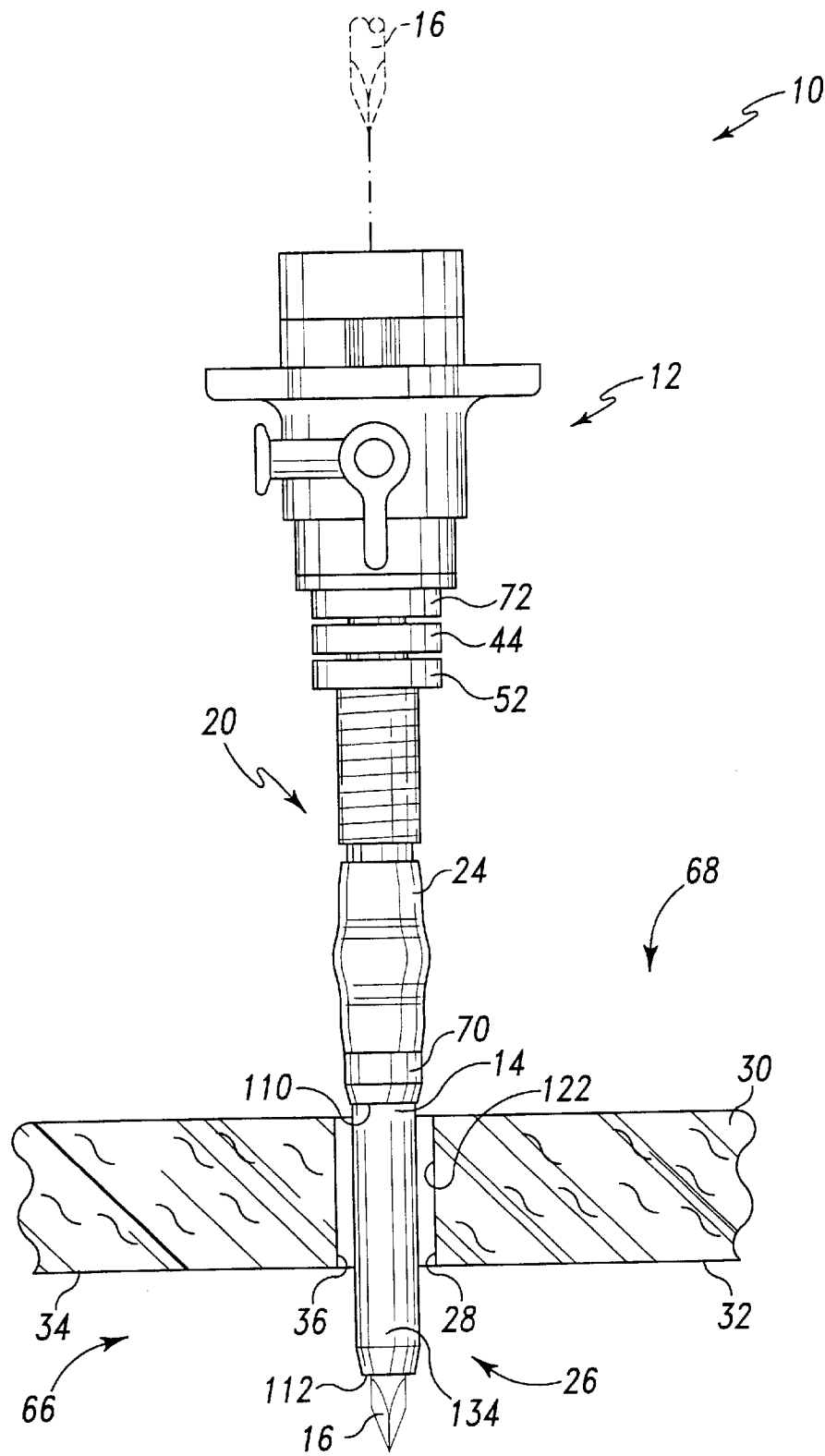
FIG. 3 is a side elevational view of the medical apparatus of FIG. 1 (note that the medical apparatus is assembled) being inserted through a body cavity wall, with the sealing member in the advancement orientation and the body cavity wall shown in cross-section for clarity of description.

Referring to FIG. 1, there is shown a medical apparatus 10 which incorporates the features of the present invention therein. The medical apparatus 10 includes a trocar assembly 12 and a sleeve 20. Trocar assembly 12 includes a cannula 14 and a trocar 16 (sometimes referred to as an "obturator"). Cannula 14 has a length $L_1$ and a lumen 18 defined therein. As shown in FIG. 3, trocar 16 is positionable between a first trocar position and a second trocar position relative to cannula 14. Trocar 16 is positioned within lumen 18 of cannula 14 when trocar 16 is positioned at the first trocar position. Trocar 16 is completely removed from lumen 18 of cannula 14 when trocar 16 is positioned at the second trocar position.

As shown in FIGS. 1, 2A, 2B, and 9, sleeve 20 includes an inner sleeve 38, an actuator 40, an outer sleeve 50, a cap 70, a support member 74 (see FIG. 2A), a locking member 52, and a sealing member 24. Note that sleeve 20 has a length $L_2$ which is less than length $L_1$ of cannula 14. Inner sleeve 38 has a passageway 22 extending therethrough and an attachment area 86 defined thereon. Inner sleeve 38 also has a knob 72 secured thereto. Inner sleeve 38 also has a groove 130 defined on an inner surface 128 of inner sleeve 38. Disposed within groove 130 is a bearing member 132, e.g. a rubber o-ring. Actuator 40 includes a middle sleeve 42 having a guide member 44 secured thereto. Middle sleeve 42 has a bore 76 defined therethrough and an attachment area 78 defined thereon. Outer sleeve 50 has channel 80 extending therethrough. Outer sleeve 50 also has an outer surface 60 with a plurality of external threads 58 defined therein. Locking member 52 has an aperture 54 defined therein. Aperture 54 has a side wall with a plurality of internal threads 82 defined therein. Cap 70 has a hole 84 extending therethrough. It should be understood that the aforementioned components of sleeve 20 can be made of any material which is compatible with being inserted into a body cavity. However, as will be discussed in detail below it is preferable that sleeve 20 be made out of an electrically conductive substance, such as metal. For example, the aforementioned components can be made of surgical steel.

Figure 2A:
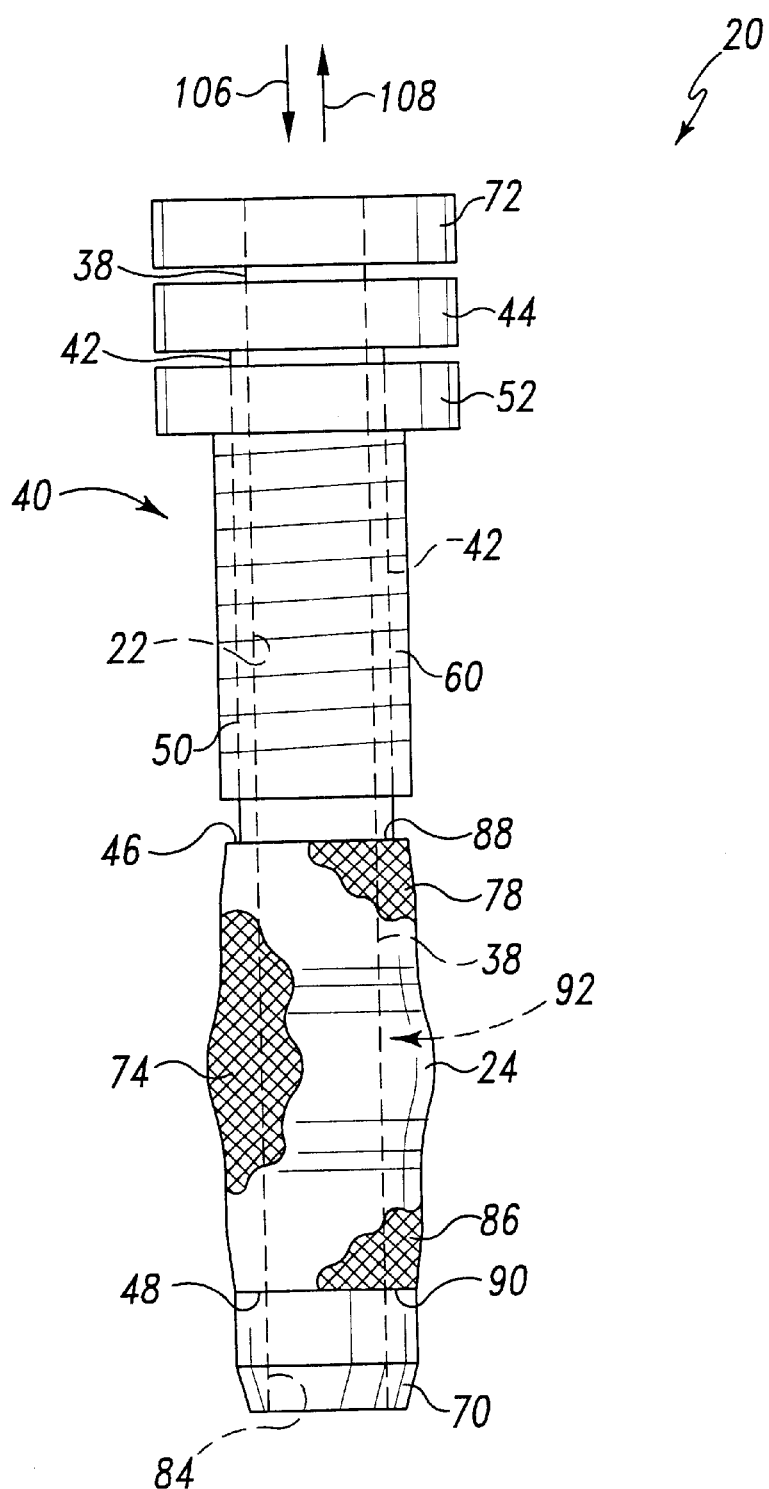
FIG. 2A is an enlarged fragmentary side elevational view of the sleeve shown in FIG. 1, with the sealing member shown in the advancement orientation.

As shown more clearly in FIG. 2A, support member 74 has the shape of a cylinder with an end 88 and an end 90. Sealing member 24 also has the shape of a cylinder with an end 46 and an end 48. Support member 74 is preferably made from a polyester PET braid material which is commercially available from Alta Technologies Inc. located in Belle Mead, N.J., as part number 95110961. Sealing member 24 is preferably made from latex tubing having about a 0.006 inch wall thickness which is commercially available from Kent Elastomer Products Inc. located in Kent, Ohio.

Figure 9:
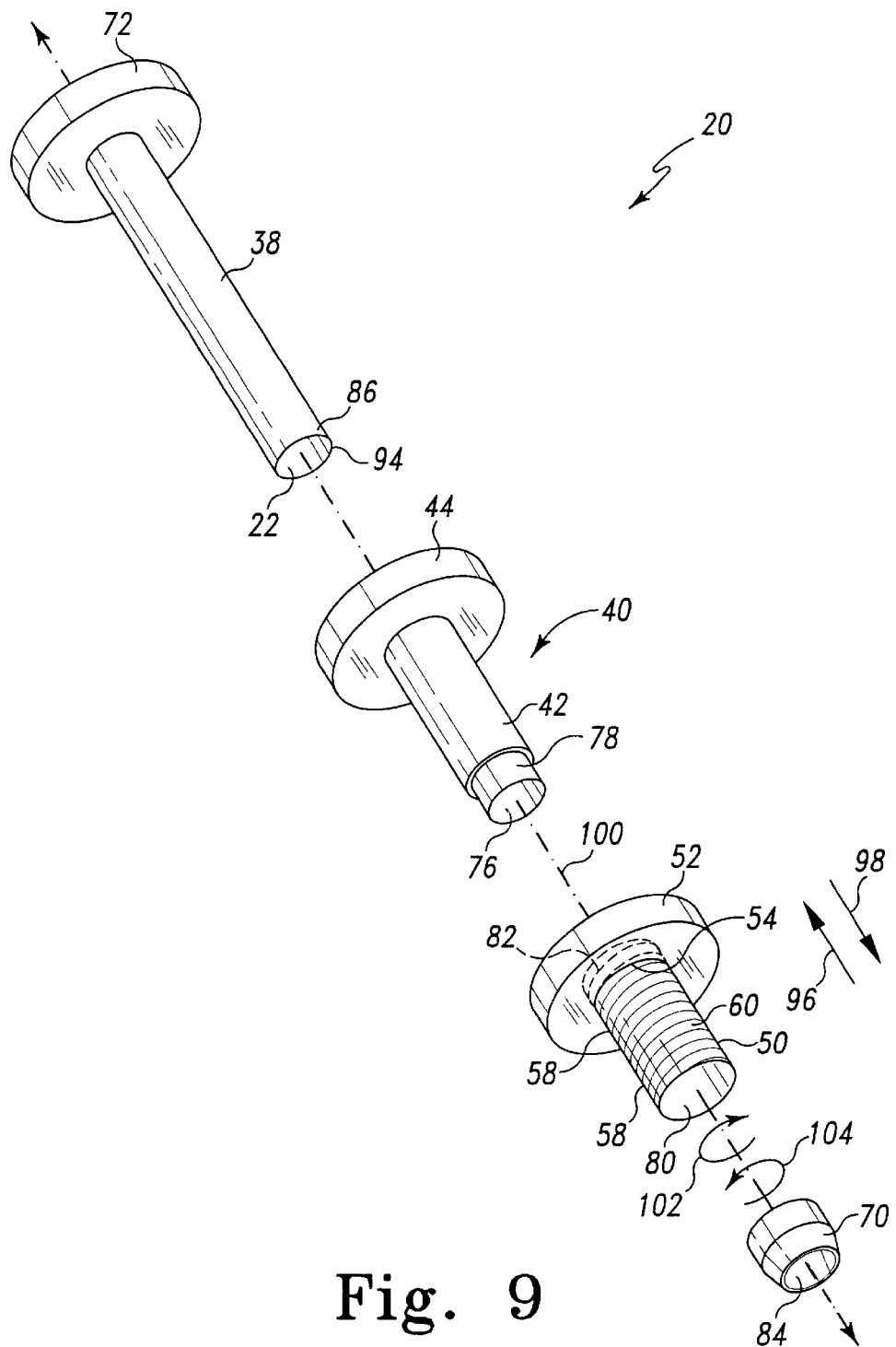
FIG. 9 is an exploded view of the sleeve of FIG. 1 (note that the support member and sealing member are not shown for clarity of description).

As shown more clearly in FIG. 9, locking member 52 is positioned relative to outer sleeve 50 such that outer sleeve 50 extends into aperture 54 and external threads 58 meshingly engage with internal threads 82 so that locking member 52 is rotatably secured to outer sleeve 50. It should be appreciated that having locking member 52 positioned relative to outer sleeve 50 in the above described manner results in locking member 52 being able to move relative to outer sleeve 50 when locking member 52 is rotated relative to outer sleeve 50. Specifically, locking member 52 can move along longitudinal axis 100 of sleeve 20 (and therefore the longitudinal axis of outer sleeve 50) in the direction indicated by arrow 96 when locking member 52 is rotated relative to outer sleeve 50 in the direction indicated by arrow 102. In addition, locking member 52 can move along longitudinal axis 100 of sleeve 20 in the direction indicated by arrow 98 when locking member 52 is rotated relative to outer sleeve 50 in the direction indicated by arrow 104.

As shown in FIGS. 2A and 9, actuator 40 is positioned relative to inner sleeve 38 such that (i) inner sleeve 38 extends through bore 76 of middle sleeve 42 and (ii) knob 72 is adjacent to guide member 44. Inner sleeve 38 and middle sleeve 42 have diameters such that middle sleeve 42 and inner sleeve 38 can easily slide relative to one another in the axial directions indicated by arrows 106 and 108. Outer sleeve 50 is positioned relative to inner sleeve 38 and actuator 40 such that (i) inner sleeve 38 and middle sleeve 42 are positioned within channel 80 of outer sleeve 50, (ii) guide member 44 is interposed between knob 72 and locking member 52, and (iii) middle sleeve 42 is interposed between inner sleeve 38 and outer sleeve 50. However, it should be understood that inner sleeve 38 has a length such that inner sleeve 38 extends out of outer sleeve 50 so as to locate attachment area 86 at a position outside of channel 80. It should also be understood that middle sleeve 42 has a length such that middle sleeve 42 extends out of outer sleeve 50 so as to locate attachment area 78 at a position outside of channel 80. It should also be understood that middle sleeve 42 and outer sleeve 50 have diameters such that outer sleeve 50 is friction fit over middle sleeve 42 so that it is relatively difficult to slide outer sleeve 50 relative to middle sleeve 42 in the axial directions indicated by arrows 106 and 108.

As shown more clearly in FIG. 2A, support member 74 is disposed around the portion 92 of inner sleeve 38 that extends out of middle sleeve 42 and outer sleeve 50. End 88 of support member 74 is secured to attachment area 78 of middle sleeve 42, whereas end 90 of support member 74 is secured to attachment area 86 of inner sleeve 38. Sealing member 24 is disposed around portion 92 and support member 74 such that support member 74 is interposed between portion 92 and sealing member 24. End 46 of sealing member 24 is secured to attachment area 78 of middle sleeve 42, whereas end 48 of sealing member 24 is secured to attachment area 86 of inner sleeve 38. The ends of support member 74 and sealing member 24 are secured in the above described manner utilizing a cyanoacrylate adhesive. Cap 70 is secured to an end 94 of inner sleeve 38 such that passageway 22 extending through inner sleeve 38 and hole 84 extending through cap 70 are linearly aligned.

As shown in FIGS. 2A, 2B, 3, and 5 sealing member 24 is movable between (1) an advancement orientation (see FIGS. 2A and 3) in which sealing member 24 is positioned to facilitate advancement of sleeve 24 into an opening 28 defined in a body cavity wall 30, and (2) a sealing orientation (see FIGS. 2B and 5) in which sealing member 24 is positioned so as to contact an interior surface 34 of a wall 30 of a body cavity 32 which surrounds a space 36 defined between opening 28 of body cavity 32 and sleeve 20. In particular, sealing member 24 is positioned in the advancement orientation by locating guide member 44 in a first position (see FIG. 2A). Alternatively, sealing member 24 can be located in the sealing orientation by locating guide member 44 in a second position (see FIG. 2B). It should be understood that in order to locate guide member 44 from the first position to the second position guide member 44 is moved in an axial direction relative to passageway 22 in a direction indicated by arrow 106 (see FIG. 2A) such that guide member 44 is moved away from knob 72. Moving guide member 44 in the above described manner causes ends 88 and 90 of support member 74 to move toward each other. In addition, moving guide member 44 in the above described manner causes end 46 of sealing member 24 to move toward end 48 of sealing member 24 such that sealing member 24 is moved from the advancement orientation to the sealing orientation. It should be appreciated that support member 74 structurally supports sealing member 24 during the above described movement such that support member 74 facilitates the movement of sealing member 24 from the advancement orientation to the sealing orientation. It should also be understood that inner sleeve 38 has a pair of leaf spring stops (not shown) attached thereto. The leaf spring stops function to prevent guide member 44 from moving in the direction indicated by arrow 108 (see FIG. 2A) once guide member 44 is located in the second position.

Figure 2B:
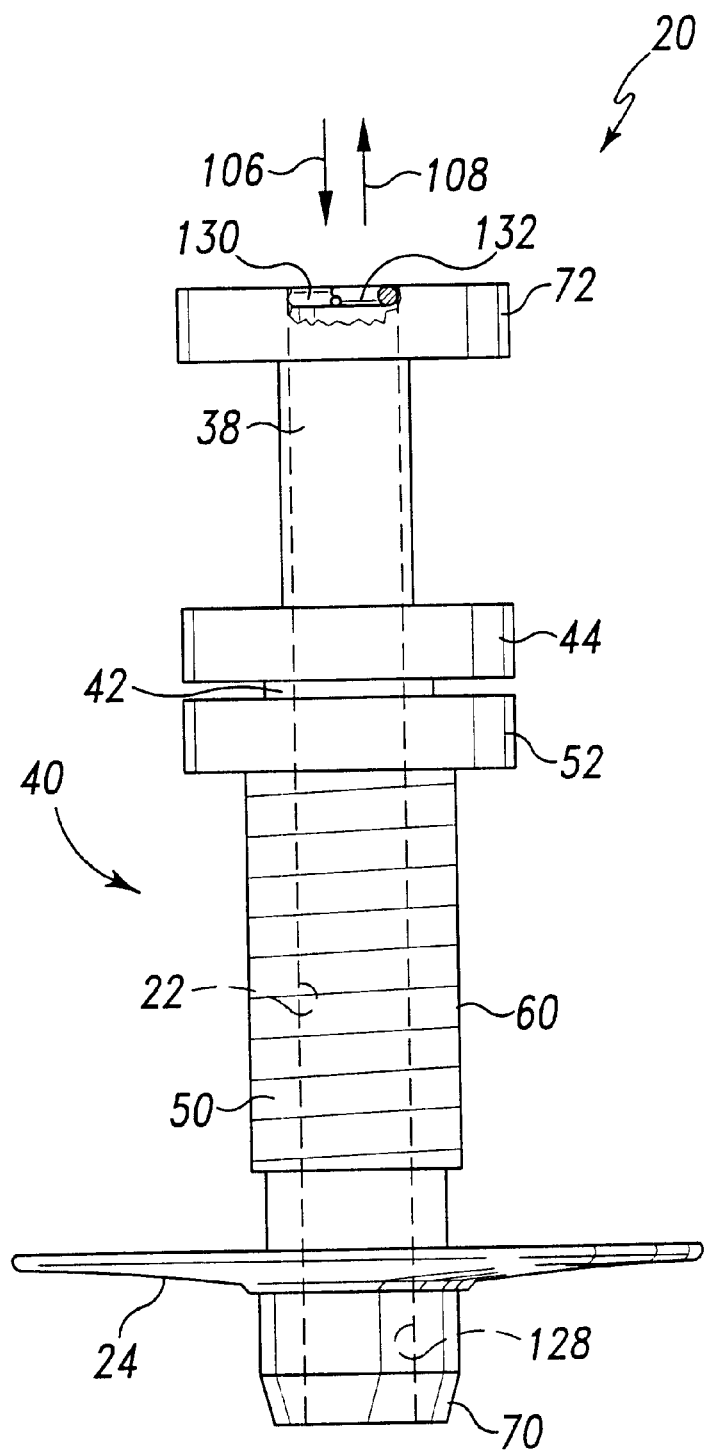
FIG. 2B is a view similar to FIG. 2A, but showing the sealing member in the sealing orientation (note that a portion of a bearing member is shown positioned within the passageway of the sleeve for clarity of description)

Sealing member 24 is moved from the sealing orientation as shown in FIG. 2B, back to the advancement orientation as shown in FIG. 2A, by moving guide member 44 from the second position to the first position. In particular, guide member 44 is rotated relative to inner sleeve 38 such that a channel (not shown) defined in guide member 44 aligns with each of the aforementioned leaf spring stops and guide member 44 is moved in an axial direction relative to passageway 22 in a direction indicated by arrow 108 (see FIG. 2B) such that guide member 44 is moved toward knob 72. Note that aligning the aforementioned channels with the leaf spring stops as described above allows guide member 44 to move past the leaf spring stops so that guide member 44 can be moved from the second position back to the first position. Moving guide member 44 in the above described manner causes ends 88 and 90 of support member 74 to move away from each other. In addition, moving guide member 44 in the above described manner causes end 46 of sealing member 24 to move away from end 48 of sealing member 24 such that sealing member 24 is moved from the sealing orientation to the advancement orientation. Thus, it should be appreciated that sealing member 24 can be repeatedly moved between the advancement orientation and the sealing orientation in the above described manner.

Figure 4:
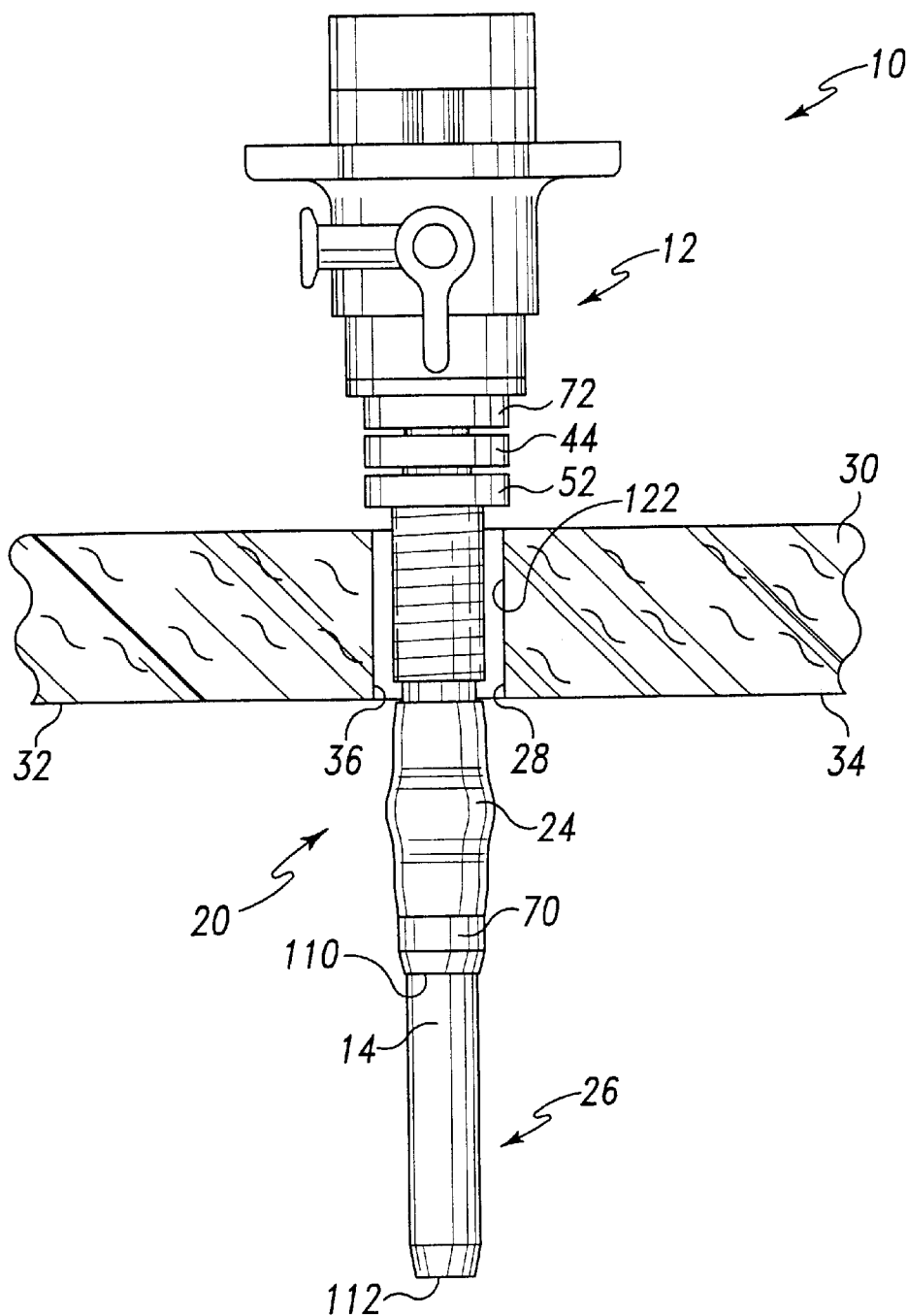
FIG. 4 is a view similar to that of FIG. 3, but showing the medical apparatus advanced further into the body cavity such that a portion of the sleeve is positioned within the opening in the body cavity wall and the sealing member is positioned within the body cavity.
Figure 5:
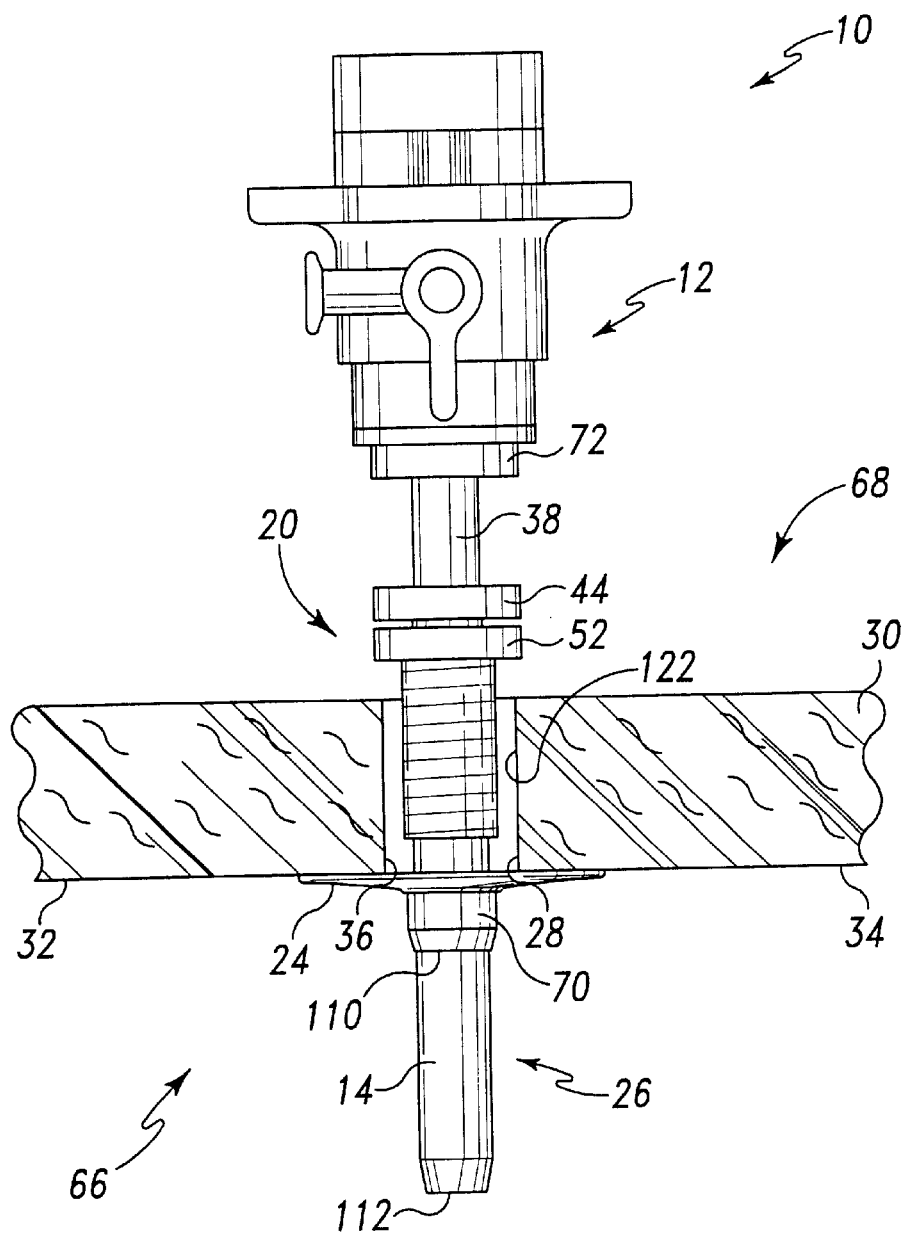
FIG. 5 is a view similar to that shown in FIG. 4, but showing the sealing member of the medical apparatus located in a sealing orientation.

As shown in FIGS. 2A–8, cannula 14 can be positioned within passageway 22 of sleeve 20 (see FIGS. 3–8) or completely removed from passageway 22. When cannula 14 is in passageway 22, an exterior surface 134 (see FIG. 3) of cannula 14 is in contact with bearing member 132 (see FIG. 2B) so as to create a fluid tight seal therebetween. Bearing member 132 is removable from groove 130 such that other bearing members (not shown) of different sizes (e.g. an o-ring having a larger or smaller cross section) can be disposed in groove 130. Placing other bearing members of different sizes in groove 130 allows sleeve 20 to accommodate instruments (e.g. a cannula) having different diameters and yet still maintain a fluid tight seal between the instrument and sleeve 20. Bearing member 132 is preferably positioned in a concentric relationship with knob 72 as shown in FIG. 2B such that bearing member 132 can be easily removed and replaced with a bearing member having a different size, as discussed above, when distal end 110 of sleeve 20 is positioned within body cavity 32 as shown in FIG. 5. Note that cannula 14 must be removed from passageway 22 before bearing member 132 can be removed and another disposed within groove 130.

Figure 6:
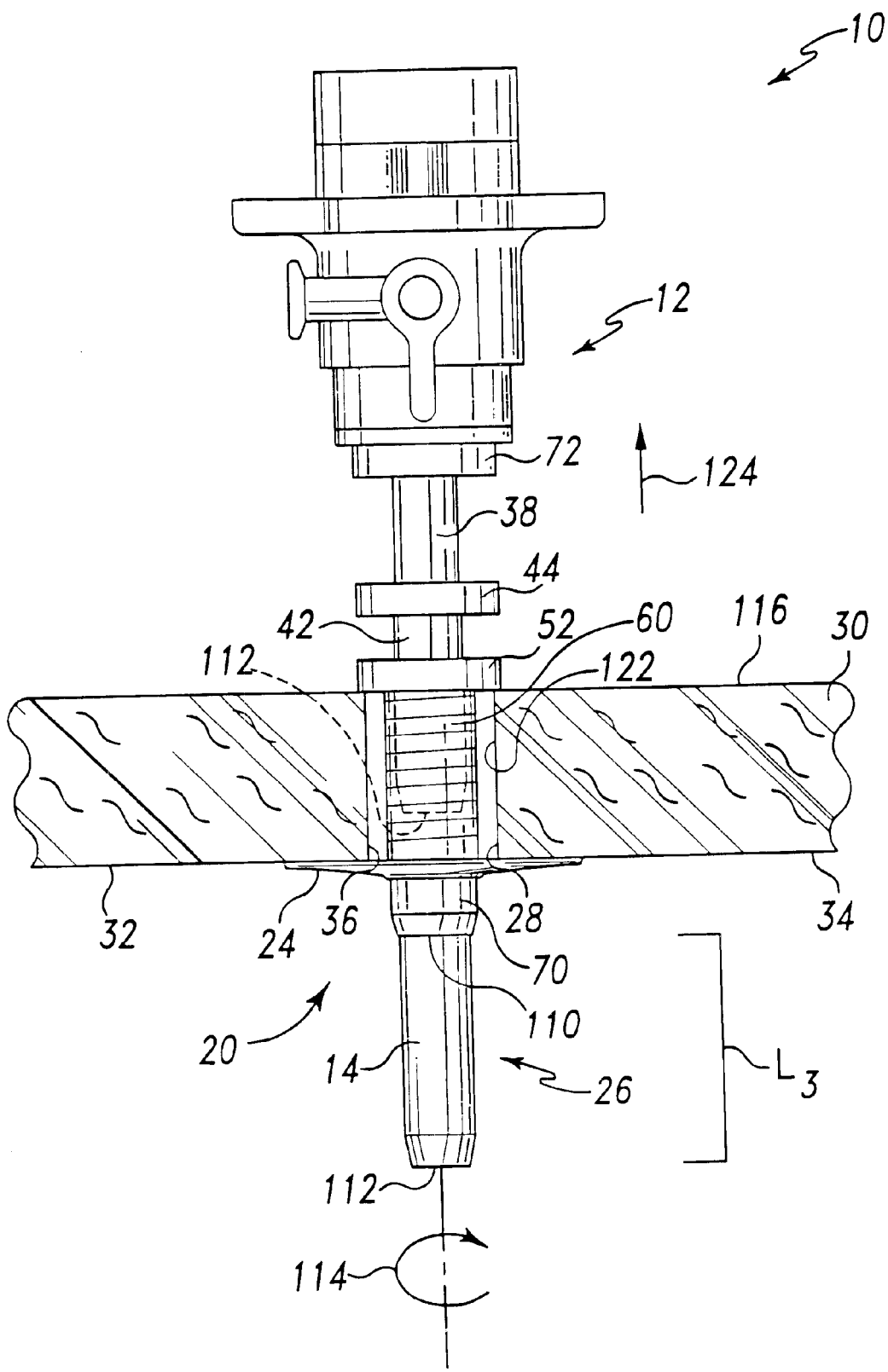
FIG. 6 is a view similar to that shown in FIG. 6, but showing a locking member of the medical apparatus positioned in contact with the body cavity wall and the cannula advanced a distance $L_3$ into the body cavity.

It should be understood that when cannula 14 is located within passageway 22 of sleeve 20, cannula 14 can be moved in an axial direction relative to sleeve 20 as indicated by arrows 106 and 108 in FIGS. 2A and 2B. Moreover, it should be appreciated that cannula 14 can be axially moved relative to sleeve 20 in the above described manner when sealing member 24 is located at the sealing orientation. Thus, it should be understood that cannula 14 is positionable between a first cannula position, a second cannula position, and a third cannula position relative to sleeve 20. Specifically, when cannula 14 is positioned at the first cannula position (see FIGS. 3–8), cannula 14 is positioned within passageway 22 of sleeve 20 such that (i) a portion 26 of cannula 14 extends out of passageway 22 of sleeve 20 and (ii) a sleeve distal end 110 is spaced apart from a cannula distal end 112. Cannula 14 is completely removed from passageway 22 of sleeve 20 when cannula 14 is positioned at the second cannula position (see FIGS. 2A and 2B). As shown in FIG. 6, cannula 14 is positioned in the third cannula position when cannula 14 is positioned relative to sleeve 20 such that cannula distal end 112 is positioned within passageway 22 of sleeve 20. It should also be understood that medical apparatus 10 can also be moved in a radial direction relative to longitudinal axis 100 (see FIG. 9) during a surgical procedure.

As shown in FIGS. 3–8, when performing a medical procedure with medical apparatus 10, such as laparoscopic surgery, trocar assembly 12 is positioned within passageway 22 of sleeve 20 as shown in FIG. 3. In addition, it is preferable that cannula 14 is positioned at the first cannula position (see FIG. 3) when trocar assembly 12 is positioned within passageway 22. Once trocar assembly 12 is placed within sleeve 20 and cannula 14 is located in the first cannula position as described, guide member 44 is placed into the first position (see FIG. 3) so that sealing member 24 is maintained in the advancement orientation. Trocar 16 of medical apparatus 10 is then placed in contact with, and advanced through, wall 30 of body cavity 32 to create opening 28 (i.e. the port site wound; note that the diameter of opening 28 is exaggerated FIGS. 3–8 for clarity of description). Preferably, sleeve 20, cannula 14, and trocar 16 are simultaneously advanced through opening 28 and into body cavity 32. It should also be appreciated that maintaining guide member 44 in its first position, and therefore sealing member 24 in the advancement orientation, facilitates the advancement of medical apparatus 10 through opening 28 and into body cavity 32. It should also be understood that having cannula 14 located in the first cannula position also facilitates the creation and advancement of medical apparatus 10 through opening 28 and into body cavity 32. Specifically, having cannula 14 positioned in the first cannula position decreases the diameter of the portion of medical apparatus 10 which is initially being advanced through opening 28. In other words, having cannula 14 in the first cannula position means only cannula distal end 112 has to be initially advanced through wall 30, rather than simultaneously advancing cannula distal end 112 and cap 70 of sleeve 20 through wall 30. Therefore, having the cannula 14 in the first cannula position decreases the force required to advance medical apparatus 10 through wall 30.

Once cannula distal end 112 enters into body cavity 32 through opening 28, trocar 16 is moved to the second trocar position (i.e. trocar 16 is completely removed from cannula 14 (see FIG. 3)). Once trocar 16 is removed, medical apparatus 10 is further advanced through opening 28 until sealing member 24 is located within body cavity 32 as shown in FIG. 4. Guide member 44 is then moved from the first position to the second position as shown in FIG. 5, thereby locating sealing member 24 in the sealing orientation. Preferably, sealing member 24 has a radius at least 6 mm greater than the outer radius of cannula 14 when sealing member 24 is in the sealing orientation. Once sealing member 24 has assumed the sealing orientation, sealing member 24 is positioned to contact interior surface 34 of wall 30 (see FIG. 5). Once sealing member 24 is in the sealing orientation and positioned in contact with interior surface 34 of wall 30 sealing member 24 surrounds a space 36 defined between opening 28 and sleeve 20. As shown in FIG. 5, positioning sealing member 24 in the above described manner prevents fluid communication between an area 66 inside of body cavity 32 and an area 68 outside of body cavity 32 through space 36.

As shown in FIG. 6, after locating sealing member 24 in the above described manner, locking member 52 is rotated relative to outer sleeve 60 in the direction indicated by arrow 114 such that locking member 52 contacts an outer surface 116 of wall 30. Placing sealing member 24 and locking member 52 in the above described manner interposes wall 30 between sealing member 24 and locking member 52 and thereby helps to stabilize medical apparatus 10 in opening 28.

Figure 7:
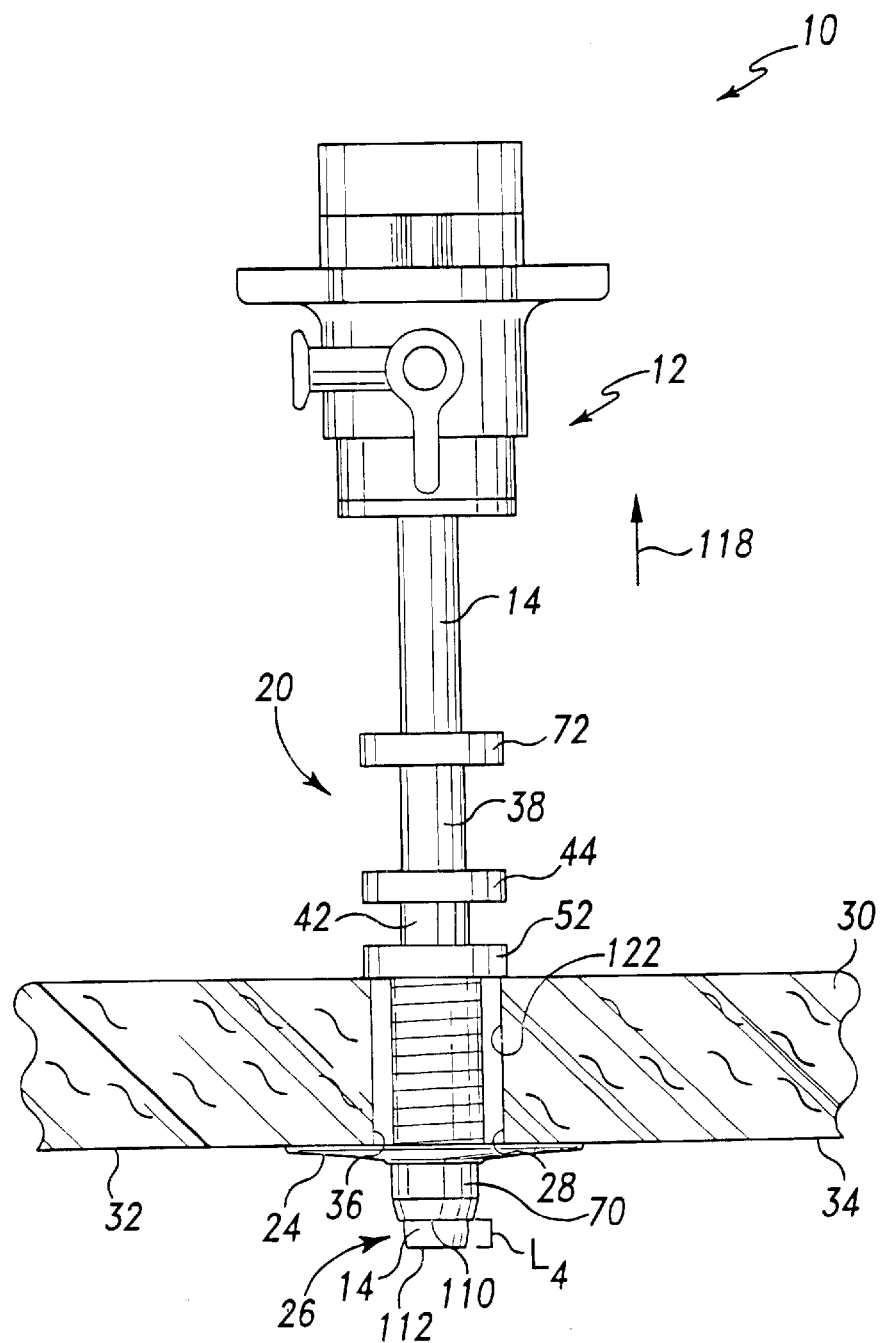
FIG. 7 is a view similar to that shown in FIG. 6, however the trocar assembly is shown inserted through the passageway of the sleeve such that the cannula is advanced to a length $L_4$ into the body cavity.
Figure 8:
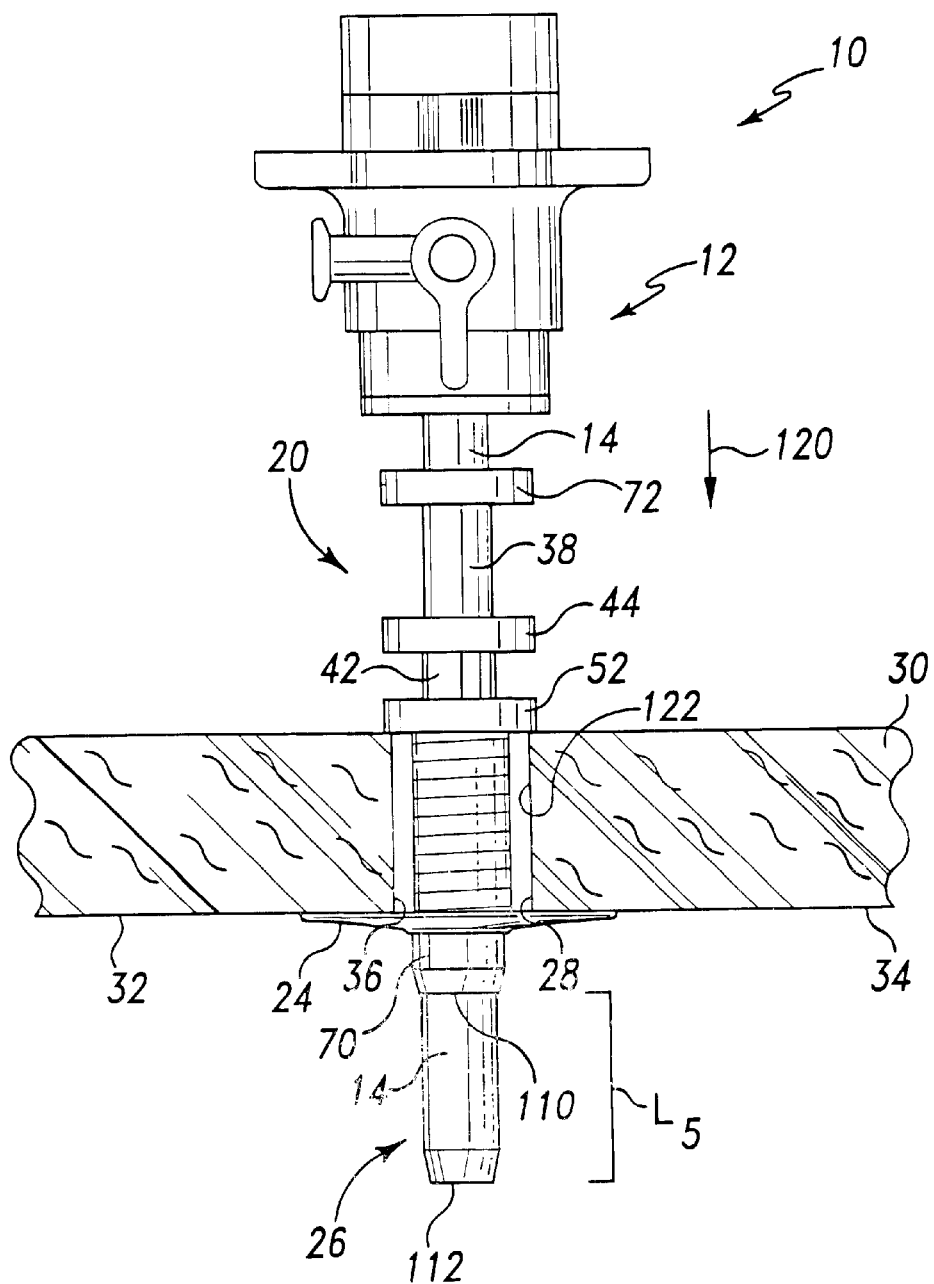
FIG. 8 is a view similar to that shown in FIG. 7, however the trocar assembly is shown inserted through the passageway of the sleeve such that the cannula is advanced to a length $L_5$ into the body cavity.

It should be appreciated that cannula 14 is slidably mounted within passageway 22 of sleeve 20. Thus, as previously discussed, the position of cannula 14 can be adjusted relative to sleeve 20. For example, as shown in FIG. 6, cannula 14 can be positioned relative to sleeve 20 such that a length $L_3$ of cannula 14 extends into body cavity 32. As shown in FIG. 7, cannula 14 can also be moved in an axial direction relative to sleeve 20 as indicated by arrow 118 such cannula 14 extends a length $L_4$ into body cavity 32. Moreover, as shown in FIG. 8, cannula 14 can be moved in an axial direction relative to sleeve 18 as indicated by arrow 120 such that cannula 14 extends a length $L_5$ into body cavity 32. Furthermore, as shown in FIG. 6, cannula 14 can be moved in an axial direction relative to sleeve 20 as indicated by arrow 124 such that cannula 14 is located in the third cannula position, i.e. cannula 14 is positioned relative to sleeve 20 such that cannula distal end 112 is positioned within passageway 22 of sleeve 20.

Being able to adjust the position of cannula 14 in the above described manner is an important aspect of the present invention since it provides a surgeon with added flexibility in moving a surgical instrument (not shown) positioned with lumen 18 of cannula 14 to the appropriate position within body cavity 32 to successfully complete a medical procedure.

In addition, it should be appreciated that cannula 14 can be moved relative to sleeve 20 in the above described manner while maintaining the contact between sealing member 24 and the interior surface 34 of body cavity wall 30. Maintaining this contact is another important aspect of the present invention since it ensures that opening 28 is protected against tumor cell implantation or contamination with an infectious agent during the above described movement of cannula 14 relative to sleeve 20. This is in contrast to the situation where a cannula cannot move in relation to the sealing member in the above described manner (i.e. the cannula and the sealing members move as a single unit). In this situation, advancing the cannula further into body cavity 32 will also advance the sealing members further into body cavity 32, thus causing the sealing members to disengage interior surface 34 of body cavity wall 30. Disengaging the sealing members from interior surface 34 allows fluid communication between an area 66 inside of body cavity and an area 68 outside of body cavity through space 36 (e.g. gas or body fluids my be advanced from an area 66 inside body cavity 32 to an area 68 outside of body cavity 32 through space 36). This fluid communication may result in tumor cells being implanted in a sidewall 122 of opening 28. The fluid communication can also result in sidewall 122 being contaminated with an infectious agent.

After completing the medical procedure utilizing medical apparatus 10, cannula 14 can be moved relative to sleeve 20 in the axial direction indicated by arrow 118 (see FIG. 7) until cannula 14 is positioned at the second cannula position (i.e. cannula 14 is completely withdrawn from passageway 22 of sleeve 20). Removing cannula 14 from sleeve 20 allows insufflation gas to rapidly escape body cavity 32 through passageway 22 of sleeve 20. Having sleeve 20 positioned within opening 28 and sealing member 20 in contact with interior surface 34 of the body cavity wall 30 protects sidewall 122 of opening 28 from coming into contact with aerosolized tumor cells or infectious agents carried by the escaping insufflation gas.

Once substantially all the insufflation gas has escaped from body cavity 32 (i.e. body cavity 32 has been desufflated) guide member 44 is moved toward knob 72 in the direction indicated by arrow 108 (see FIG. 2B) so as to position guide member 44 in the first position as shown in FIG. 2A. The movement of guide member 44 to the first position forces sealing member 24 to be placed in the advancement orientation (see FIG. 2A), thereby facilitating the removal of sleeve 20 from opening 28.

Thus, it should be understood that sleeve 20 including sealing member 24 is the last component to be removed from body cavity 32 by the surgeon (not shown). Removing sleeve 20 including sealing member 24 last ensures that opening 28 (i.e. the port site wound) remains protected against tumor cell implantation or contamination with an infectious agent until completion of the medical procedure.

It should be appreciated that the probability of contaminating opening 28 with infectious or cancerous cells during a medical procedure is much greater when trocar assembly 12 is not equipped with sleeve 20. Specifically, when trocar assembly 12 is not equipped with sleeve 20, an exterior surface of cannula 14 can come into direct contact with sidewall 122 of opening 28. This direct contact can result in the contamination of opening 28 since tumor cells and infectious agents have been shown to become adhered to the exterior surface of a cannula during a medical procedure. Therefore, as cannula 14 is moved in and out of opening 28 in the absence of sleeve 20, tumor cells and/or infectious agents adhered to the exterior surface thereof are brought into direct contact with sidewall 122 of opening 28. The aforementioned direct contact can result in tumor cells being implanted into sidewall 122, or sidewall 122 being contaminated with an infectious agent. However, having trocar assembly 12 equipped with sleeve 20, as shown in FIGS. 3–8, provides a barrier between sidewall 122 and cannula 14 which prevents tumor cells from coming into contact with, and thus becoming implanted into, sidewall 122. In addition, the barrier provided by sleeve 20 prevents sidewall 122 from becoming contaminated with an infectious agent.

As discussed above, when electrosurgical techniques are used in conjunction with laparoscopic techniques an active electrode is typically passed through a nonconducting plastic or fiberglass cannula, or a metal cannula used in conjunction with a nonconductiong collar, this arrangement results in a tube within a tube across which a difference in electrical potential exists. As a result, when current is passed through the active electrode, the cannula itself becomes a capacitor. Thus, when a part of the cannula comes into contact with an internal organ such as the intestine, a pin-point burn may result at the point of contact which can have serious consequences for the patient. However, having all of the components of sleeve 20, except for sealing member 24 and support member 74, made from an electrically conductive substance, such as 303 stainless steel, prevents the aforementioned problem. In particular, having sleeve 20 made from a conductive material is an advantage since it allows sleeve 20 to act as an electrical conductor. Having sleeve 20 capable of acting as an electrical conductor prevents the cannula from becoming a capacitor by allowing electrical current to harmlessly flow from the active electrode to the electrically grounded patient (via wall 30 (see FIG. 5) which is in contact with sleeve 20). Thus, utilizing a sleeve 20 which is made from an electrically conductive material (e.g. metal) in the above described manner reduces the electrosurgical injuries typically associated with employing electrosurgical techniques in conjunction with laparoscopic techniques.

Based upon the above description it will be understood by those skilled in the art that the present invention provides a medical apparatus for protecting a port site wound which adds only a minimal amount of bulk to the diameter of a trocar assembly. In addition, it will be understood by those skilled in the art that the present invention provides a medical apparatus for continuous protection of a port site wound which enables the independent movement of a cannula or trocar assembly, thus allowing the surgeon to functionally utilize the cannula and instruments to their fullest design. Moreover, it will be understood by those skilled in the art that the medical apparatus of the present invention can be retrofit to existing trocar assembly technology. Furthermore, the medical apparatus of the present invention allows minimally invasive surgical techniques, such as laparoscopic surgery, to be safely applied to cancer surgery. In addition, the medical apparatus of the present invention prevents the electrosurgical injuries typically received when electrosurgical techniques are used in conjunction with laparoscopic techniques.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected. For example, rather than having locking member 52 rotatably mounted onto outer sleeve 60, locking member 52 can be integral to outer sleeve 60 such that rotation of locking member 52 causes the rotation of outer sleeve 60 so that outer sleeve 60 is screwed into opening 28.

What is claimed is:

1. A medical apparatus insertable into an opening defined in a wall of a body cavity, comprising:
    a trocar assembly comprising a trocar and a cannula, said cannula having a lumen adapted to removably receive said trocar;
    a sleeve adapted to be removeably disposed within the opening in the wall of the body cavity, said sleeve including a passageway adapted to receive said cannula and a sealing member, said sealing member being adjustable between an advancement orientation for advancing the sleeve into said opening and a sealing orientation in which said sealing member sealingly contacts an interior surface of the wall circumferentially surrounding the opening, said cannula being slideably movable within said passageway when said sealing member is in said sealing orientation and removable from said passageway, and said sealing member movable between said advancement orientation and said sealing orientation with said cannula being received in said passageway.

2. The medical apparatus of claim 1 further comprising an actuator operatively coupled with said sealing member, said sleeve and said actuator relatively movable for selectively adjusting said sealing member to provided said sealing and said advancement orientations.

3. The medical apparatus of claim 2 wherein said sleeve has a longitudinal axis directed substantially parallel to said passageway and said sealing member has a first portion attached to said actuator, a second portion attached to said sleeve, and a third flexible portion extending between said first and second portions, said actuator and said sleeve relatively movable along said longitudinal axis for selectively placing said third flexible portion of said sealing member in said advancement and sealing orientations.

4. The medical apparatus of claim 3 wherein relative movement of said actuator relative to said sleeve in a first axial direction decreases the axial separation between said first and second portions of said sealing member so that said third portion has a first diameter in said advancement orientation and relative movement of said actuator relative to said sleeve in a second axial direction increases the axial separation between said first and second portions of said sealing member so that said third portion has a second diameter in said sealing orientation, said second diameter greater than said first diameter.

5. The medical apparatus of claim 4 wherein said second diameter is larger than a diameter of the opening in the wall of the body cavity and the second diameter is equal to or less than the diameter of the opening.

6. The medical apparatus of claim 2 wherein said sleeve has a longitudinal axis directed substantially parallel to said passageway, said sleeve includes a first tubular member and a second tubular member telescopically received within said first tubular member, and said actuator and said first tubular member are relatively movable in a direction parallel to said longitudinal axis for selectively providing said sealing and said advancement orientations of said sealing member.

7. The medical apparatus of claim 3 wherein said actuator includes a third tubular member positioned between said first and second tubular members of said sleeve, said third tubular member affixed to said second tubular member and said third tubular member movable relative to said second tubular member of said sleeve in a direction parallel to said longitudinal axis.

8. The medical apparatus of claim 4 wherein said sealing member has a first portion attached to said third tubular member of said actuator, a second portion attached to said second tubular member of said sleeve, and a third flexible portion extending between said first and second portions such that relative axial movement between said second and third tubular members selectively places said third flexible portion of said sealing member in said advancement and sealing orientations.

9. The medical apparatus of claim 2 wherein said sealing member comprises a flexible inner support member and a flexible outer tubular member surrounding said inner support member, said inner support member having a first end attached to said actuator and a second end attached to said sleeve and relative movement of said sleeve and said actuator causes said inner support member and said outer tubular member to expand outwardly so that a portion of said tubular member sealingly contacts the interior surface of the wall circumferentially surrounding the opening.

10. The medical apparatus of claim 1 wherein said cannula has a length $L_1$ and said sleeve has a length $L_2$ shorter than said length $L_1$ such that a portion of said cannula extends out of said passageway of said sleeve when said cannula is received in said passageway.

11. The medical apparatus of claim 1 wherein said sleeve further comprises a locking member having a threading engagement with an exterior portion of said sleeve, said lock member disposed outside of the wall of the body cavity, and rotation of said locking member relative to said sleeve in a direction to advance said locking member toward the wall of the body cavity causing said locking member to contact an exterior surface of the wall circumferentially surrounding the opening to thereby capture the wall between said sealing member and said locking member.

12. The medical apparatus of claim 1 wherein said sleeve has a longitudinal axis directed substantially parallel to said passageway and said sealing member includes flexible portion having a first diameter in said advancement orientation and a second diameter in said sealing orientation, said second diameter being larger than a diameter of the opening in the wall of the body cavity and the second diameter being equal to or less than the diameter of the opening.

13. The medical apparatus of claim 1 wherein said sealing member comprises a flexible inner support member and a flexible outer tubular member supported by and concentric with said inner support member.

14. The medical apparatus of claim 13 wherein said inner support member has a braided structure.

* * * * *